(12) United States Patent
Kidmose et al.

(10) Patent No.: US 10,959,639 B2
(45) Date of Patent: Mar. 30, 2021

(54) EEG MONITORING APPARATUS AND METHOD FOR PRESENTING MESSAGES THEREIN

(75) Inventors: Preben Kidmose, Marslet (DK); Soren Erik Westermann, Humlebak (DK)

(73) Assignee: T&W Engineering A/S, Lynge (DK)

( * ) Notice: Subject to any disclaimer, the term of this patent is extended or adjusted under 35 U.S.C. 154(b) by 333 days.

(21) Appl. No.: 13/335,896

(22) Filed: Dec. 22, 2011

(65) Prior Publication Data
US 2012/0165695 A1 Jun. 28, 2012

Related U.S. Application Data

(63) Continuation-in-part of application No. PCT/DK2009/050147, filed on Jun. 26, 2009.

(51) Int. Cl.
*A61B 5/0476* (2006.01)
*A61B 5/0482* (2006.01)
*A61B 5/00* (2006.01)

(52) U.S. Cl.
CPC .......... *A61B 5/0476* (2013.01); *A61B 5/0482* (2013.01); *A61B 5/6815* (2013.01); *A61B 5/6838* (2013.01); *A61B 5/7232* (2013.01); *A61B 2560/0276* (2013.01)

(58) Field of Classification Search
USPC ................................................. 600/544, 545
See application file for complete search history.

(56) References Cited

U.S. PATENT DOCUMENTS

| | | | | |
|---|---|---|---|---|
| 4,395,740 A | * | 7/1983 | Yuen | G09B 5/065 360/134 |
| 4,828,501 A | * | 5/1989 | Ingenito | G09B 23/288 434/262 |
| 5,577,510 A | * | 11/1996 | Chittum | A61B 5/0002 600/519 |
| 6,354,299 B1 | | 3/2002 | Fischell et al. | |

(Continued)

FOREIGN PATENT DOCUMENTS

| | | |
|---|---|---|
| JP | 2007-94474 A | 4/2007 |
| JP | 2007-516783 A | 6/2007 |

(Continued)

OTHER PUBLICATIONS

International Search Report for PCT/DK2009/050147 dated Mar. 24, 2010.

(Continued)

*Primary Examiner* — Etsub D Berhanu
(74) *Attorney, Agent, or Firm* — Sughrue Mion, PLLC

(57) ABSTRACT

An EEG monitoring apparatus (2) adapted to be carried continuously by a person being monitored comprises means adapted for measuring at least one EEG signal from the person carrying the apparatus and a signal processing means for analysing said at least one EEG signal and adapted to identify or predict predetermined biological incidents in said person based on said analysis. The EEG monitoring apparatus (2) further comprises a decision means adapted to decide when information is to be presented to said person and a message selection means for selecting a voice message providing said person with information, as well as an acoustic transducer adapted for presenting the selected voice message to the person. The invention also provides a method for presenting voice messages.

25 Claims, 4 Drawing Sheets

(56) References Cited

U.S. PATENT DOCUMENTS

| | | | |
|---|---|---|---|
| 7,224,777 B1* | 5/2007 | Tannenbaum | H04M 1/72547 340/309.16 |
| 2002/0013538 A1* | 1/2002 | Teller | A61B 5/0002 600/549 |
| 2003/0050536 A1* | 3/2003 | Hood | A61B 5/021 600/300 |
| 2003/0070182 A1* | 4/2003 | Pierre | H04N 5/76 725/135 |
| 2003/0130590 A1* | 7/2003 | Bui | A61B 5/0002 600/537 |
| 2005/0027182 A1* | 2/2005 | Siddiqui | A61B 5/14532 600/365 |
| 2005/0085799 A1* | 4/2005 | Luria | A61B 5/6803 606/1 |
| 2005/0129252 A1* | 6/2005 | Heintzman et al. | 381/58 |
| 2006/0224319 A1* | 10/2006 | Rogers | G06Q 10/109 701/516 |
| 2006/0281980 A1* | 12/2006 | Randlov et al. | 600/301 |
| 2007/0106126 A1* | 5/2007 | Mannheimer | A61B 5/14551 600/300 |
| 2007/0208262 A1 | 9/2007 | Kovacs | |
| 2007/0287931 A1* | 12/2007 | Dilorenzo | 600/545 |
| 2008/0069365 A1* | 3/2008 | Shuttleworth et al. | 381/57 |
| 2008/0119702 A1* | 5/2008 | Reggiardo | A61B 5/14532 600/345 |
| 2008/0159555 A1* | 7/2008 | Asada et al. | 381/71.11 |
| 2008/0192966 A1* | 8/2008 | Pape | 381/312 |
| 2008/0208073 A1* | 8/2008 | Causevic | A61B 5/048 600/544 |
| 2009/0062678 A1* | 3/2009 | Beck-Nielsen | 600/544 |
| 2009/0062682 A1 | 3/2009 | Bland et al. | |
| 2009/0222852 A1* | 9/2009 | Bartolome | 725/33 |
| 2010/0125212 A1* | 5/2010 | Kim | A61B 5/022 600/485 |
| 2011/0130665 A1* | 6/2011 | Bowers | A61B 5/02055 600/483 |
| 2011/0193704 A1* | 8/2011 | Harper | A61B 5/14532 340/573.1 |

FOREIGN PATENT DOCUMENTS

| | | |
|---|---|---|
| WO | 2005/065538 A2 | 7/2005 |
| WO | WO 2006066577 A1 | 6/2006 |
| WO | 2007/144307 A2 | 12/2007 |

OTHER PUBLICATIONS

OA for Japanese Patent Application 2012-515354 dated Oct. 1, 2013, with English Translation.

Office Action for Japanese Patent Application No. 2012-515354 dated Jun. 4, 2013, with English translation.

Communication dated Sep. 12, 2018, from Intellectual Property of India in counterpart application No. 10116/DELNP/2011.

* cited by examiner

EEG MONITORING APPARATUS AND METHOD FOR PRESENTING MESSAGES THEREIN

The present application is a continuation-in-part of application PCT/DK2009/050147, filed on Jun. 26, 2009, in Denmark and published as WO 2010/149157 A1.

BACKGROUND OF THE INVENTION

1. Field of the Invention

The present invention relates to a portable EEG monitoring apparatus. The invention, more particularly, relates to a portable EEG monitoring apparatus adapted to be carried continuously by a person. The invention furthermore relates to a method of presenting messages in such a portable EEG monitoring device.

EEG is the commonly used abbreviation for Electro EncephaloGram, EEG monitoring is generally speaking a method of electrically monitoring brain activity of a person. Systems for monitoring EEGs have been known for many years. However with the general technological development, EEG monitoring systems, which may be carried or worn continuously by a person to be monitored, have been devised.

2. The Prior Art

One such system is known from the document WO-A1-2006/066577, where blood sugar levels are monitored in a person suffering from diabetes in order to warn against hypoglycaemic attacks. Low blood sugar levels have severe influences on the brain activity and too low blood sugar levels may lead to unconsciousness and even death. The system disclosed WO-A1-2006/066577 is a fully implanted subcutaneous system. The implanted electrodes are via electrical leads connected to a monitoring device capable of detecting the brainwaves characteristic for an imminent hypoglycaemic attack, and issuing a warning in the form of a vibration of the subcutaneous monitoring device. In WO-A1-2006/066577 it is furthermore suggested that the implant may wirelessly communicate with an external unit, which may contain the more power demanding parts of the electronics, so as to obtain a long battery service life of the implanted subcutaneous parts. It is stated that this will also allow an acoustic warning, but WO-A1-2006/066577 does not disclose any details on how.

Other systems known from e.g. US-A1-2009/0062682 or US-B-6354299 suggest monitoring of brain states using an implant, and the use of voice messages to warn against disorders, such as imminent epileptic seizures, based on the monitored brain states.

Based on this prior art it is a feature of the present invention, to provide an improved system vis-à-vis the prior art system, in particular regarding the acoustic warning of the person carrying the apparatus.

SUMMARY OF THE INVENTION

The invention, in a first aspect, provides a portable EEG monitoring apparatus, said apparatus comprising: EEG pick-up means adapted for measuring at least one EEG signal from the person carrying the apparatus, a signal processing means for analysing said at least one EEG signal and adapted to identify or predict predetermined biological incidents in said person based on said analysis, a decision means adapted to decide when information is to be presented to said person, a message selection means for selecting a voice message providing said person with information, and an acoustic transducer adapted for presenting the selected voice message to the person, where said apparatus is adapted to present the voice message in the ear of the person.

The invention, in a second aspect, provides a method for presenting voice messages in a portable EEG monitoring apparatus, said method comprising measuring at least one EEG signal from the person carrying the apparatus using an EEG pick-up means; analysing said at least one EEG signal using a signal processing means adapted to identify or predict predetermined biological incidents in said person based on said analysis; deciding, using a decision means, when information is to be presented to said person; selecting, using a message selection means, a voice message for providing said person with information; and presenting, in the ear of the person, the selected voice message to the person using an acoustic transducer.

Using a voice message rather than, e.g. a simple warning tone, has many advantages. A major advantage, however, is that a voice message, such as a spoken warning is far more pervasive in getting the attention of the person addressed, and far easier for the person to respond correctly to. Bearing in mind that the purpose of the EEG monitoring is in first instance to warn the person about threatening biological incidents such as imminent hypoglycaemic seizure, it is very likely that the warning issued by the apparatus is issued at a time where the person is already no longer at his full mental capacity, or even on the verge of unconsciousness. A voice message is in this situation not only far more efficient in alerting the person, but may moreover actually contain direct instructions regarding the corrective actions to be performed, in order to avoid the threatening condition. Thus, the person who may already be partially mentally incapacitated, will not only get an alarm at a time where he is no longer capable of remembering what the correct corrective actions are and how to perform these, but will get a voice message reminding him of the appropriate corrective actions.

According to a preferred embodiment said voice message relates to said biological incident.

Presenting the message directly in the ear of the user is advantageous in that it reduces external disturbances such as ambient noise. Moreover, it is advantageous in that it allows the EEG monitoring apparatus to further comprise the functionalities of a hearing aid, or to form part of a hearing aid.

According to a preferred embodiment of the first aspect of the invention, said voice messages are stored in the apparatus. Storing the voice messages in the apparatus obviates the need of carrying any further devices, or the need of a synthetic voice generator.

According to a further preferred embodiment of the first aspect of the invention, the voice messages are formatted into a format suitable for storage and replay in the apparatus. This reduces the need for storage space, and may thus allow for an overall size reduction, or the storage of a larger variety of voice messages.

According to another embodiment of the first aspect of the invention, said voice messages have been edited in accordance with the hearing capabilities of said person. Editing the voice messages allow built-in adaptation of the messages to a specific hearing loss of the person. This, in turn, increases the intelligibility of the voice message.

According to yet another embodiment of the first aspect of the invention, the apparatus comprises means for adjusting the presented voice message to the current ambient acoustic noise level when presenting the message. This further enhances intelligibility of the message.

According to a further embodiment of the first aspect of the invention, the apparatus comprises means for allowing the person carrying the apparatus to store messages therein in accordance with the persons own choice. This allows the person carrying the apparatus to choose straight forward easy to understand messages.

According to another embodiment of the first aspect of the invention, the apparatus comprises means for the person carrying the apparatus to acknowledge the presented message. Hereby it becomes possible to ensure that the person carrying the apparatus has actually heard the message, and if necessary repeat the message until it has been acknowledged, possibly with increased volume.

According to yet another embodiment of the first aspect of the invention, the apparatus is further adapted to present voice messages relating to the handling of the apparatus. This aids the person carrying the apparatus in the handling and use thereof, e.g. when placing the apparatus in the ear.

Embodiments of the method according to the second aspect of the invention generally provide the same advantages as the embodiments according to the first aspect.

BRIEF DESCRIPTION OF THE DRAWINGS

The invention will now be described in greater detail based on non-limiting exemplary embodiments and the drawing, on which.

DETAILED DESCRIPTION OF THE INVENTION

Figure 1:
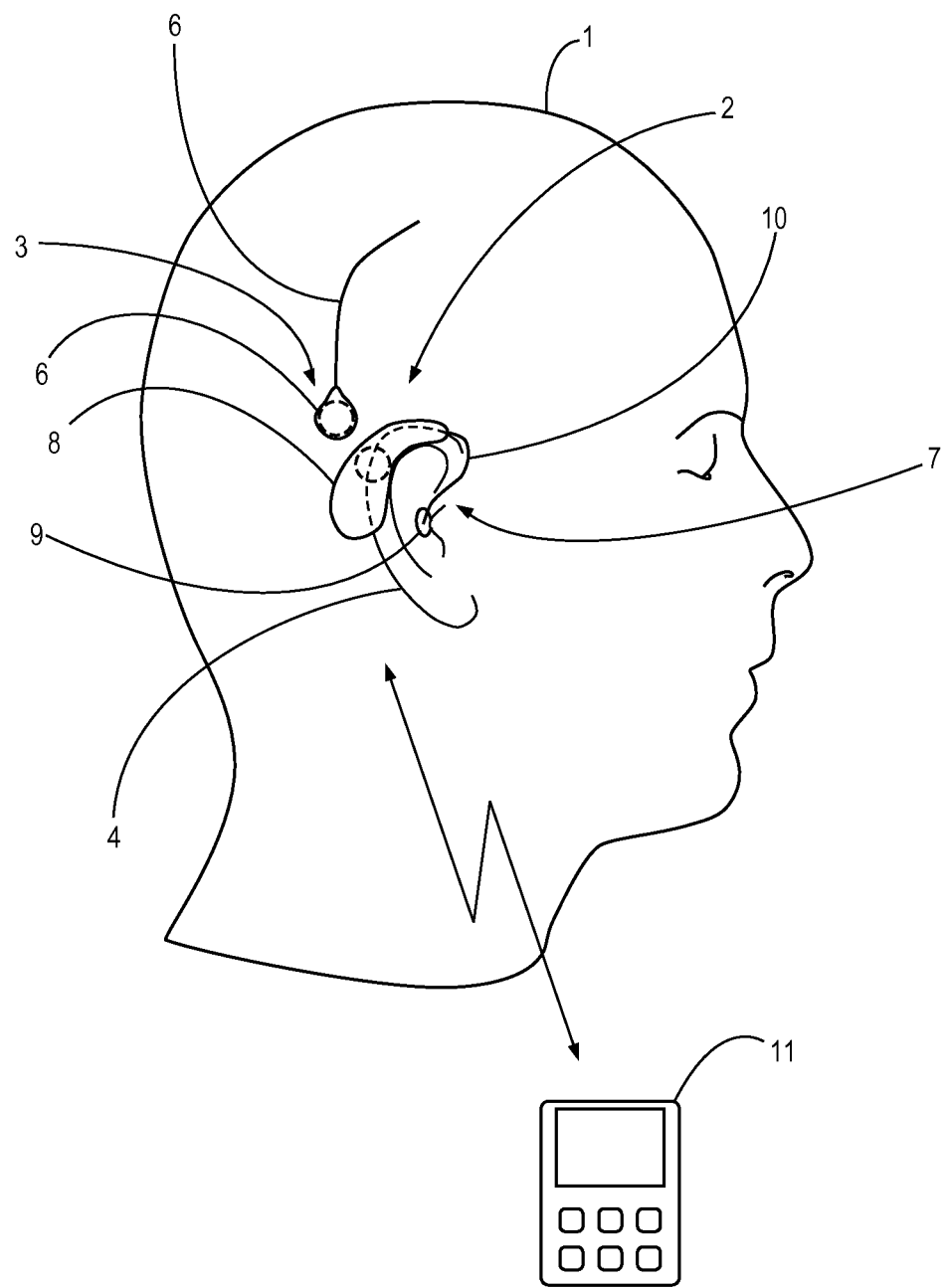
FIG. 1 depicts a head of a person with an EEG monitoring apparatus according to an embodiment of the invention.

FIG. 1 schematically shows a head 1 of a person carrying an EEG monitoring apparatus 2 according to an embodiment of the invention. The EEG monitoring apparatus 2 comprises an implant unit 3 for measuring EEG's. The implant unit 3 is located subcutaneously behind the ear 4 of a person. The implant unit 3 comprises an electronics part 5 and an EEG pick-up means 6 such as probe with at least two electrodes (not shown) for picking up electrical EEG signals from the brain of the person. The electronics part 5 of the implant unit 3 comprises the necessary electronics for sampling the EEG signals measured by the electrodes of the EEG pick-up means 6 and transmitting them wirelessly to an external unit 7 forming part of the EEG monitoring apparatus 2. Preferably, the energy supply to the implant unit 3 is received inductively from the external unit 7, so that the implant unit 3 has a long service life, not constrained by battery capacity, which is advantageous since a replacement of the battery would necessitate a surgical procedure for replacement of the whole implant unit 3.

As can be seen, the external unit 7 may resemble a Behind-The-Ear hearing aid (BTE hearing aid), comprising a housing part 8, which in normal use is placed behind an ear 4 of the person carrying the EEG monitoring apparatus 2. Like a BTE hearing aid, the housing part 8 is connected to an earplug 9 in the ear canal of the person via an intermediate connection 10. This could be a traditional sound tube leading to an earplug, or an electrical cord leading to a Receiver In The Ear type earplug (RITE earplug). This allows the external unit 7 to give off messages, such as alarms or warnings, into the ear 4 of the person carrying the EEG monitoring apparatus 2.

As indicated, the EEG monitoring apparatus 2 may optionally include a peripheral device 11, which, as will be explained later, may comprise additional and possibly more energy consuming electronic storage space for data.

Figure 2:
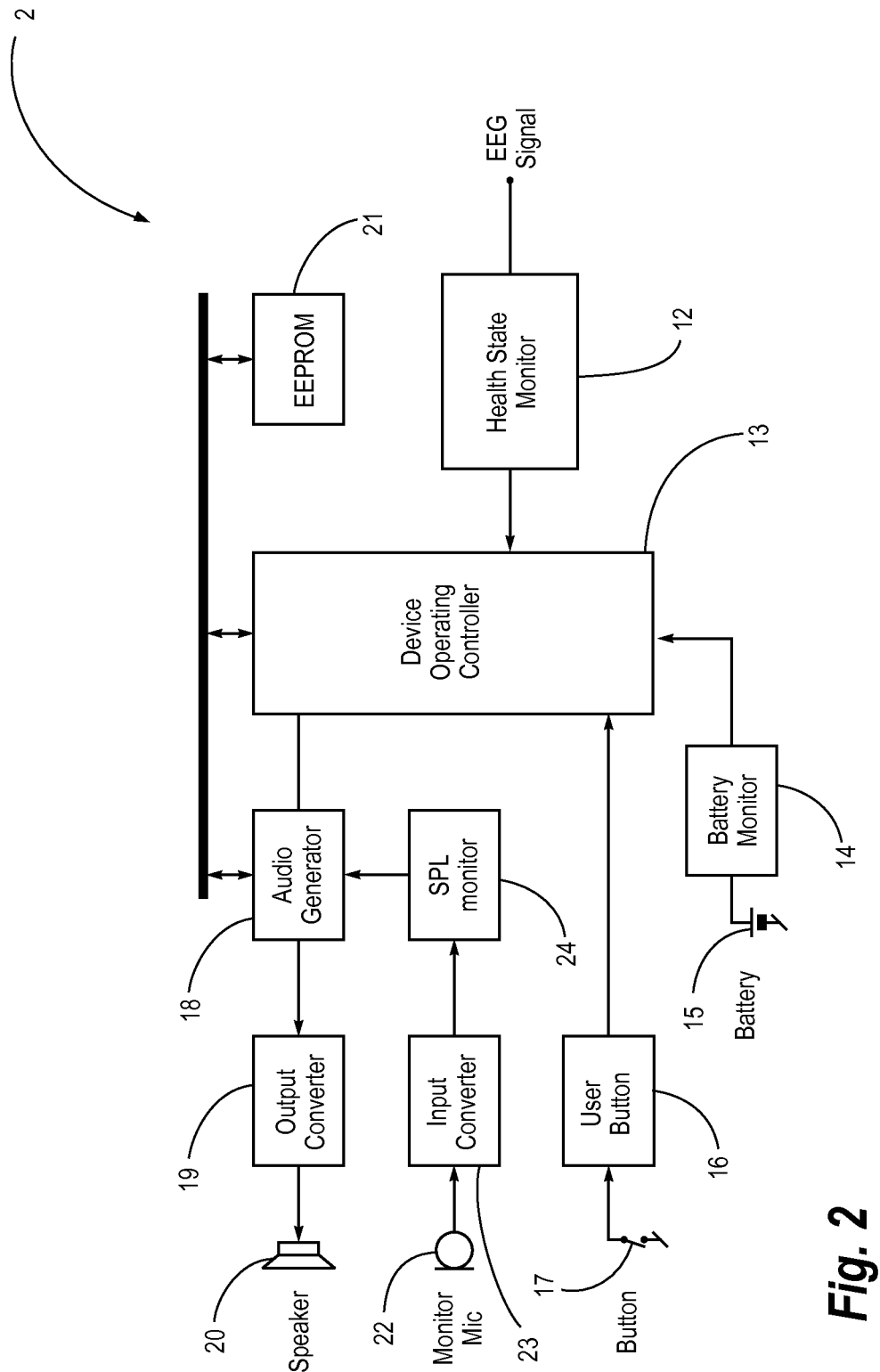
FIG. 2 depicts a block diagram of the EEG monitoring apparatus according to FIG. 1.

Turning now to FIG. 2, the internal details of the external unit 7 of the EEG monitoring apparatus 2 are schematically shown. The external unit 7 comprises a health state monitor 12, comprising means for analysing an EEG signal received wirelessly from the implant unit 3, and for detecting anomalies in said EEG signal, in order to warn the person carrying the EEG monitoring apparatus 2 against health threatening conditions, such as e.g. hypoglycaemia or epileptic seizures. How this analysis is performed is not relevant for the present invention and will not be dealt with any further.

If a health threatening condition is detected, the health state monitor 12 sends an appropriate signal to a device operating controller 13. The device operating controller 13 is also adapted for receiving other input such as a signal indicating low battery level from a battery monitor 14 monitoring the battery 15 supplying the EEG monitoring apparatus 2, and a user input signal from a user button 16 comprising e.g. an electromechanical key switch 17.

The device operating controller 13 selects an appropriate message and settings for the message and sends a corresponding signal to an audio generator 18, which generates a message signal for an output converter 19, such as a DAC generating an output signal for an output transducer, such as a loudspeaker 20. As indicated above the loudspeaker could be placed in the housing 8 of the external device or it could be placed in the earplug 9, but it should be noted that the present invention is not limited to the use in BTE type devices, it could also be implemented in an In-The-Ear earplug (ITE earplug) or any other type of earplug known e.g. from hearing aids. The message signal or data relating thereto may pre stored in a non-volatile memory, such as an EEPROM 21.

Preferably, the EEG monitoring apparatus 2 also comprises means for monitoring ambient sound pressure level. In the illustrated embodiment, such means comprise a monitor microphone 22 delivering a signal to an input converter 23 such as an ADC. The input converter 23 delivers a signal to a sound pressure level monitor 24. The sound pressure level monitor 24 detects the ambient sound pressure level, and delivers a corresponding signal to the audio generator, 18, allowing the audio generator to adapt the volume settings for the signal to the output converter 19 in accordance with the ambient sound pressure level. Thus, it is ensured that the message signal delivered by the loudspeaker 20 has a volume level allowing it to be easily heard by the person carrying the EEG monitoring apparatus 2. At the same time it is ensured that the message is not presented with an excessive loudness in quiet surroundings, which could be both disturbing and uncomfortable for the person carrying the EEG monitoring apparatus 2. Evidently, the sound pressure level monitor need not be operative at all times. It is sufficient to sample the current sound pressure level for just a short time before presenting the message. Thus, power is saved.

Figure 3:
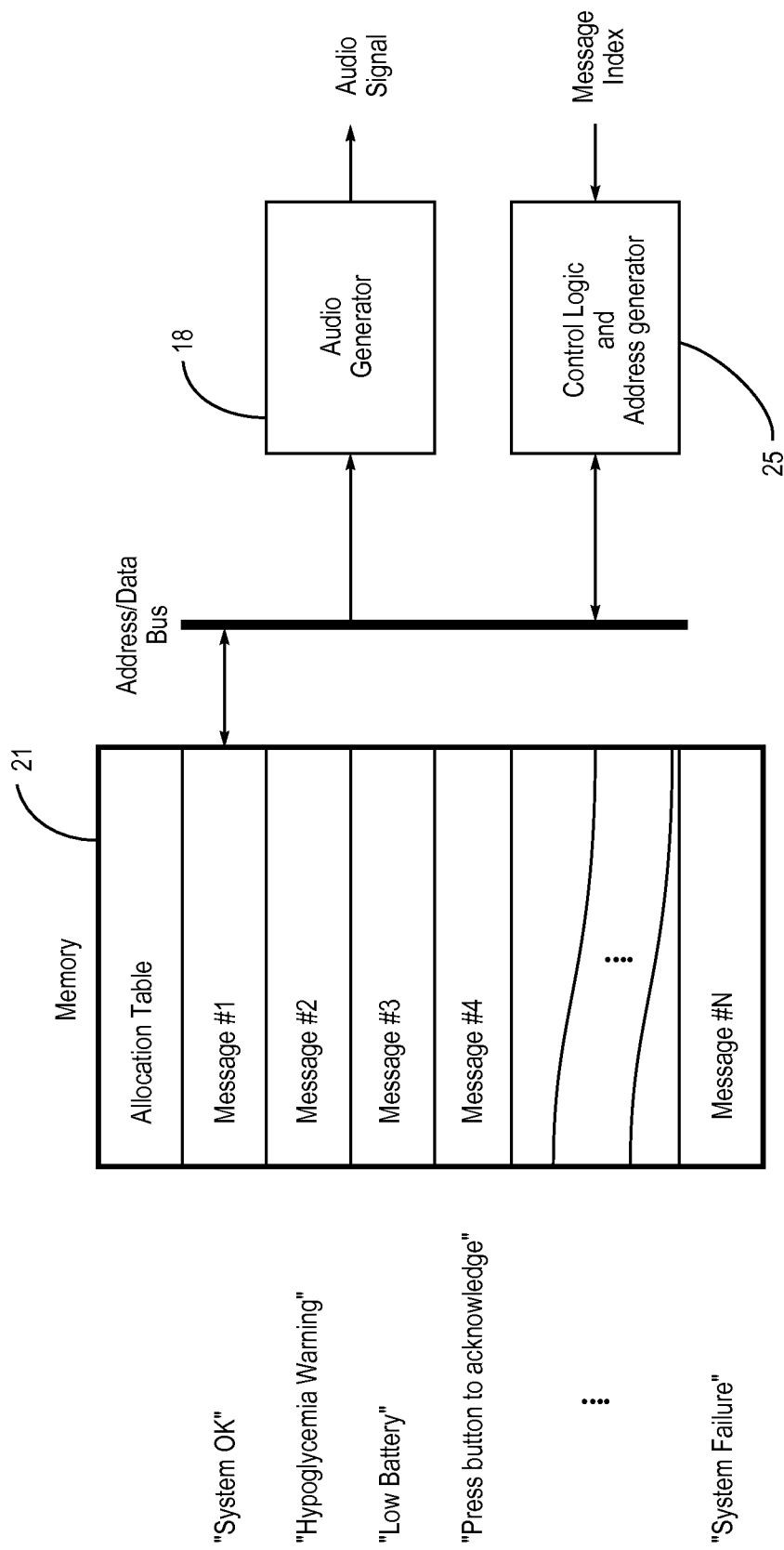
FIG. 3 illustrates the storage and retrieval of messages in the EEG monitoring apparatus of FIG. 2.

FIG. 3 illustrates various messages stored in the non-volatile memory 21. Only five messages are illustrated, i.e. messages #1 to #4 and the last message #N, comprising typical warnings, such as "System OK", "Hypoglycaemia Warning", "Low Battery", "Press button to acknowledge" and "System Failure". These messages are retrieved from the non-volatile memory 21 by means of a control logic and address generator 25 in the device operating controller 13, addressing a desired message, or rather the data defining it, in the non-volatile memory and causing the corresponding message data to be sent to the audio generator 18, which produces the output signal to the output converter 19 on the basis thereof.

Depending on considerations such as the available storage, power consumption etc., the data defining the desired message and stored in the non-volatile memory may differ.

One way of storing the messages would be uncompressed digital audio, where the entire data stream necessary for the audio generator 18 to generate the signal to the output converter 19 is stored. In that case the audio generator 18 could generate a pulse code modulated signal for the output converter 19, which turns the pulse code modulated signal into an analog signal. However, because the dynamic range of speech is quite wide, the pulse code modulated signal could be a weighted signal such as an A-law or MU-law weighted signal, where the dynamic range is compressed before storage. The audio generator 18 would in that case also perform a corresponding expansion of the message signal.

An alternative could be compressed audio as is known from speech or audio codecs, where the compressed data signal is stored as data in the memory. Examples of such speech and audio codecs are; MPEG-1 (mp3), described in the standard ISO/IEC-11172 part 3, DPCM (Differential Pulse Code Modulation), ADPCM (Adaptive Differential Pulse Code Modulation), described in the standard ITU G.726, subband-ADPCM as described in the standard ITU G.722, or speech codecs as described in standards ITU G.729 or ITU G.728.

Also, instead of compressed audio based on a real speech signal, synthetic speech could be used. Synthetic speech can be generated from symbol-linguistic representations, such as phonemes or other symbol representation of basic building blocks of a speech signal. In that case these symbols are stored in the non-volatile memory 21, and the audio generator comprises a synthesizer, which synthesizes waveform signals based on the symbols. Such synthesizing will typically be based on a mapping from the symbol representation to waveform signals based on segments of a sampled speech signal.

In addition to the above methods, or possibly a combination thereof, the EEG monitoring apparatus may also comprise means for generating non-speech sounds, such as simple sounds like pure tones, or "pling", "boing", "bleep" or the like or sounds resembling musical instruments. Such sounds may be generated by an audio generator 18 comprising one or more tone generators and/or filters, e.g. impulse response filters or simple filters.

Figure 4:
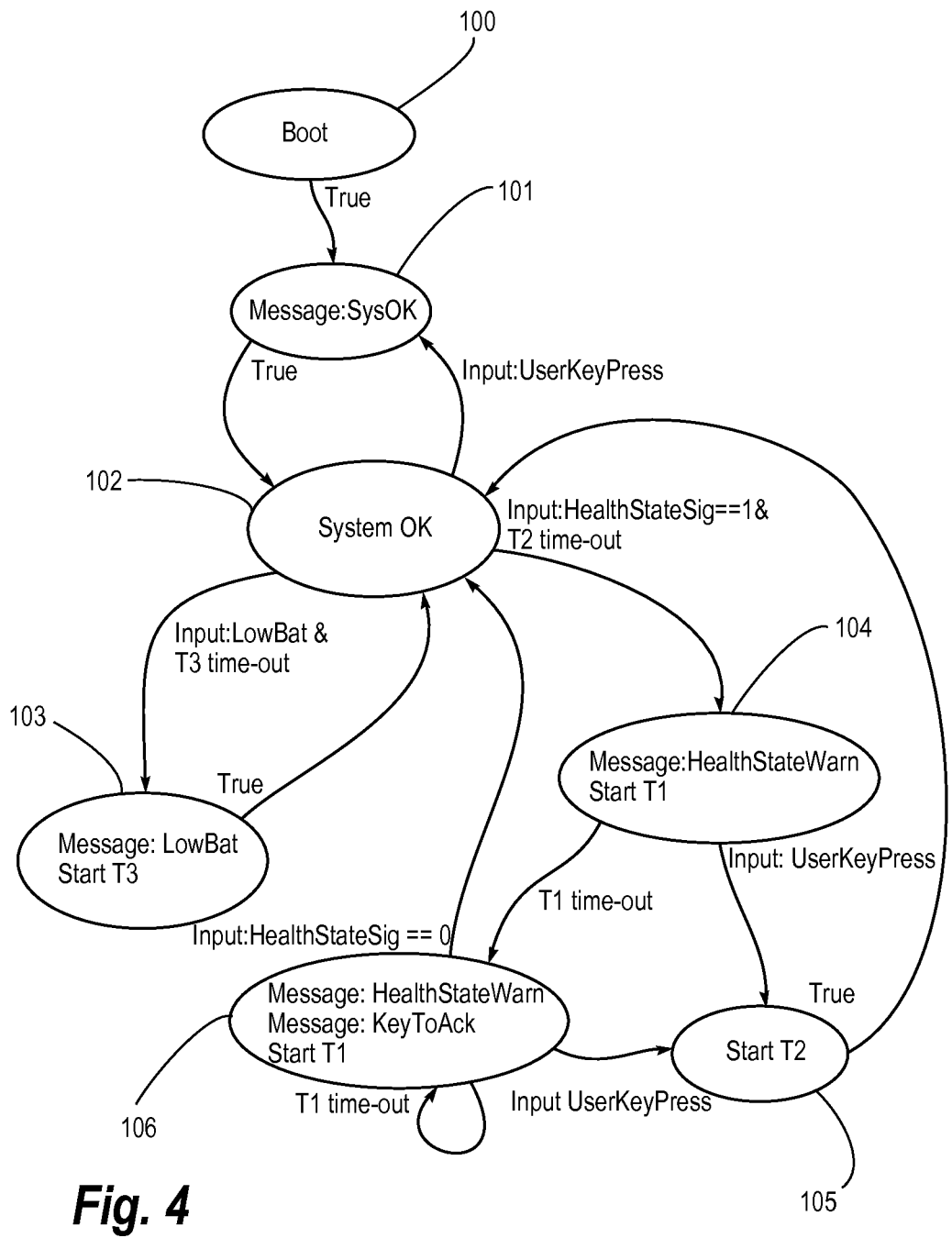
FIG. 4 depicts a state diagram of the user interface of the EEG monitoring apparatus according to FIG. 2.

FIG. 4 shows a state diagram of the user interface of the EEG monitoring apparatus according to the invention. The diagram is simplified to illustrate only the most essential messages, but as will be understood from FIG. 3 there can be many more messages, adding of course to the complexity of the interface.

In FIG. 4 the following texts are used:

| Message Mnemonic | Message |
|---|---|
| SysOK | "System OK" |
| LowBat | "Low battery" |
| HealthStateWarn | "Hypoglycaemia warning" |
| KeyToAck | "Press key to acknowledge" |

| Timer | Timer Usage |
|---|---|
| T1 | Timer for repeating unacknowledged messages |
| T2 | Timer for repeating warnings from health state monitor |
| T3 | Battery alarm timer |

| User Interface Input | Description |
|---|---|
| UserPressKey | User key press |
| LowBat | Low battery signal from battery monitor |
| HealthStateSig | Signal from health state monitor |

The state diagram of FIG. 4 will now be described. However, for full explanation, reference to apparatus parts not shown in FIG. 4 is also made in the following description. Please refer to FIGS. 1 and 2 for those reference numerals not found in FIG. 4.

Starting at the top of FIG. 4 the EEG monitoring apparatus 2 boots in box 100 when switched on. During booting, the EEG monitoring apparatus performs a number of self-tests, such as testing the functioning of the electrodes of the EEG pick-up means 6, and the communication link between the implant unit 3 and the external device 7. If the self-test is successful a true flag is set and, in box 101, the device operating controller 13 sends SysOK to the audio generator 18, which retrieves the message "System OK" in the non-volatile memory and presents it to the person carrying the EEG monitoring apparatus 2, via the output converter 19 and the speaker 20. The person carrying the EEG monitoring apparatus 2 thus receives confirmation that the EEG monitoring apparatus 2 is operating and functional. After the "System OK" message has been sent, the EEG monitoring apparatus 2 enters its normal state in box 102. In box 102, the person wearing the EEG monitoring apparatus can at any time activate the user push button 16 by pressing the key switch 17, which will lead to a new self-test and message in box 101.

If at any time the battery monitor 14 detects low battery, it sends the low battery signal, LowBat, to the device operating controller 13, or preferably sets it high as a flag for the device operating controller 13 to detect. Provided a timer T3 is not running, the device operating controller 13 sends LowBat to the audio generator 18, which retrieves the message "Low battery" in the non-volatile memory and, in box 103, presents it to the person carrying the EEG monitoring apparatus 2, via the output converter 19 and the speaker 20. At the same time the timer T3 is started. If the timer T3 is still running, i.e. has not timed out, LowBat is not sent to the to the audio generator. By proper selection of the time value of T3, the person carrying the EEG monitoring apparatus is thus prevented from hearing the "low battery" messages so frequently that it annoys him. Thus, at intervals corresponding to T3 the person carrying the EEG monitoring apparatus is repeatedly reminded to change the battery. When he eventually does so, the EEG monitoring apparatus 2 boots again in box 100.

If at any time the health state monitor 12 detects imminent hypoglycaemia, it sends the hypoglycaemia warning signal, HealthStateSig, to the device operating controller 13, or preferably sets it high as a flag for the operating controller 13 to detect. Provided a timer T2 is not running, the device operating controller 13 sends HealthStateWarn to the audio generator 18, which retrieves the message "Hypoglycaemia warning" in the non-volatile memory and, in box 104, presents it to the person carrying the EEG monitoring apparatus 2 via the output converter 19 and the speaker 20. At the same time a timer T1 is started. If the person carrying the EEG monitoring apparatus 2 activates the user push button 16 by pressing the key switch 17, the device operating controller receives the input UserKeyPress, which acknowledges that the user has heard the message presented to him. At the same time the timer T2 is started in box 105. If, in box 102, the timer T2 is still running, i.e. has not timed out, the user interface does not proceed from box 102 to 104, and the person carrying the EEG monitoring apparatus is thus prevented from hearing the "Hypoglycaemia warning", messages so frequently that it annoys him, if he knows he does not yet need to take action or he is not in a position to take such action.

If the person carrying the EEG monitoring apparatus 2 does not acknowledge the message "Hypoglycaemia warning", the timer T1 will eventually time out and the interface will proceed from box 104 to 106. In box 106, the device operating controller 13 sends HealthStatWarn and KeyToAck to the audio generator 18, which sequentially retrieves the messages "Hypoglycaemia warning" and "Press key to acknowledge" and presents them to the person carrying the EEG monitoring apparatus 2 via the output converter 19 and the speaker 20. At the same time the timer T1 is restarted. These two messages will then be repeated at intervals corresponding to the value of T1, which is preferably relatively short compared to T2, until either the person carrying the EEG monitoring apparatus 2 eventually activates the user push button 16 by pressing the key switch 17, or the signal or flag HealthStateWarn goes low, e.g. because the person carrying the EEG monitoring device has taken appropriate actions. In the former case, the interface proceeds to box 105, where the timer T2 is started, and back to box 102 where it remains until T2 times out as described above. In the latter case where HealthStateSig goes low, there is no danger any more and the interface returns to box 102 where it remains until changes occur. That is to say until the flags HealthStateSig or LowBat go high again, or until the user activates the push button 16 by pressing the key switch 17 in order to perform a self-test.

With such a user interface the EEG monitoring apparatus 2 gives off the alarm or warning to the person wearing the EEG monitoring apparatus 2, and does this repeatedly until the person has heard and responded to the warning. Since the alarm or warning is related to a life threatening condition it may be important to repeat the message frequently. A typical value for T1 could thus be less than a minute, e.g. 15 seconds. A typical value for T2, where the person carrying the EEG monitoring apparatus 2 has acknowledged the messages and is expected to take proper action, should be longer, e.g. several minutes. A typical value for T2 could be 10 to 15 minutes. T3 for the battery alarm could depending of the criteria selected for the battery alarm be longer e.g. 1 to 2 hours or more.

In order to ensure that the person carrying the EEG monitoring apparatus 2 is not just missing the message by not hearing it, the volume could be increased with each repetition until it is acknowledged.

Though the interface above has been described only in relation to a simple structure with a few warning messages, the skilled person will realise that means for providing access to further messages could be realised, e.g. by activating the push button 16 by repeatedly pressing the key switch 17 twice or multiple times. The signal sent from the push button 16 to the device operating controller 13 could depend on the number of times the key switch 17 is pressed. This could gain access to menu points and messages, where more data is provided to the person carrying the EEG monitoring apparatus 2. This is particularly interesting if the EEG data is logged over time. In such cases the user may learn more about when he typically has many warnings or the like. Also, it may provide access to the settings of the EEG monitoring apparatus 2, e.g. allowing the user to change alarm threshold, warning intervals, volume settings etc. Furthermore, the user may even use the menu to upload information externally to the peripheral device 11, with larger storage capacity, so as to store information about his daily behaviour in terms of blood sugar, so as to keep a diary about events and the like, or event to learn how to modify his behaviour.

The invention has been described above with reference to various specific embodiments. However, as is readily appreciated by a person skilled in the art, other embodiments than the ones disclosed above are equally possible within the scope of the invention, as defined by the appended patent claims. In particular the skilled person will realise that instead of using a subcutaneous implant, it will also be possible to implement the messages in a fully external EEG monitoring apparatus, e.g. in an earplug or BTE device using external electrodes in contact with the skin, as well as in an external EEG monitoring apparatus having a wired connection to the implant.

The skilled person will also realise that sufficient electronic storage space may be provided in the EEG monitoring apparatus to store generic speech messages which may be altered or interchanged with other messages by means of a peripheral device 11 such as a mobile telephone.

Messages may also be provided for guiding the person carrying the EEG monitoring device through the mounting process, when he puts it on and starts carrying it.

We claim:

1. A portable EEG monitoring apparatus, said apparatus comprising:
    an EEG pick-up component configured to measure at least one EEG signal from a person carrying the apparatus,
    a signal processor configured to analyze said at least one EEG signal and to identify or predict a predetermined biological incident in said person based on said analysis,
    a decision component configured to decide when information is to be presented to said person, wherein said information is one of first and second types, wherein said decision component decides that information of said first type relates to a health state and should be presented to said person only after a first interval (T2) has elapsed since information of said first type was last presented to and acknowledged by said person, and decides that information of said second type should be presented to said person only after a second interval (T3) has elapsed since information of said second type was last presented to said person, and said first interval is shorter than said second interval,
    a message selector configured to select a voice message from amongst plural voice messages for providing said person with the information, and
    an acoustic transducer for presenting the selected voice message to the person as a spoken voice message, where
    said apparatus is adapted to present the selected voice message in the ear of the person,
    said apparatus further comprising an acknowledgement component whereby the person carrying the apparatus can acknowledge the presented spoken voice message, the spoken voice message being repeated until it is acknowledged, and wherein when said information to be presented relates to a health state of said person, said spoken voice message is repeated until acknowledged, at a repeat interval (T1) of duration less than said first interval.

2. The EEG monitoring apparatus according to claim 1, wherein said selected voice message relates to said biological incident.

3. The apparatus according to claim 1, wherein said plural voice messages are stored in the apparatus.

4. The apparatus according to claim 1, wherein said plural voice messages are formatted into a format suitable for storage and replay in the apparatus.

5. The apparatus according to claim 1, wherein said plural voice messages have been edited in accordance with the hearing capabilities of said person.

6. The apparatus according to claim 1, comprising a message modification component configured to adjust the presented voice message to the current ambient acoustic noise level when presenting the voice message.

7. The apparatus according to claim 1, comprising a message storage component configured to allow the person carrying the apparatus to store messages therein in accordance with the person's own choice.

8. The apparatus according to claim 1, further adapted to present voice messages relating to the handling of the apparatus.

9. The apparatus according to claim 8, wherein said messages relating to the handling of the apparatus comprise messages to guide the person through a process of putting on the apparatus.

10. The portable EEG monitoring apparatus, according to claim 1,
wherein the identified or predicted biological incident is a hypoglycaemic seizure in said person, and
wherein said message selector is configured to select a voice message providing said person with information including instructions regarding actions to be performed in order to avoid hypoglycaemic seizure.

11. The apparatus according to claim 1, wherein said presented spoken voice message relates to the identified or predicted predetermined biological incident, and wherein said apparatus further comprises an element operable by said person to trigger at least one further voice message relating to said identified or predicted predetermined biological incident.

12. The apparatus according to claim 1, wherein said spoken voice message is repeated a plurality of times at increasing volume at each repetition until acknowledged.

13. A method for presenting voice messages in a portable EEG monitoring apparatus, said method comprising:
measuring at least one EEG signal from a person carrying the apparatus using an EEG pick-up component;
analyzing said at least one EEG signal using a signal processing component configured to identify or predict a predetermined biological incident in said person based on said analysis;
deciding, using a decision component, when information is to be presented to said person, wherein said information is one of first and second types, wherein said decision component decides that information of said first type relates to a health state and should be presented to said person only after a first interval (T2) has elapsed since information of said first type was last presented to and acknowledged by said person, and decides that information of said second type should be presented to said second person only after a second interval (T3) has elapsed since information of said second type was last presented to said person, and said first interval is shorter than said second interval;
selecting, using a message selector, a voice message from amongst plural voice messages for providing said person with the information,
presenting, in the ear of the person, the selected voice message to the person as a spoken voice message using an acoustic transducer; and
repeating said selected voice message until said person acknowledges said presented message, wherein when said information to be presented relates to a health state of said person, said spoken voice message is repeated until acknowledged, at a repeat interval (T1) of duration less than said first interval.

14. The method according to claim 13, wherein said selected voice message relates to said biological incident.

15. The method according to claim 13, wherein said plural voice messages are stored in the apparatus.

16. The method according to claim 13, wherein said plural voice messages are formatted into a format suitable for storage and replay in the apparatus.

17. The method according to claim 13, wherein said plural voice messages are edited in accordance with the hearing capabilities of said person.

18. The method according to claim 13, wherein the presented voice message is adjusted to the current ambient acoustic noise level when presenting the voice message.

19. The method according to claim 13, wherein messages are stored in accordance with the person's own choice.

20. The method according to claim 13, wherein the person carrying the apparatus is required to acknowledge the presented message.

21. The method according to claim 13, wherein voice messages relating to the handling of the apparatus are also presented.

22. The method according to claim 21, wherein said messages relating to the handling of the apparatus comprise messages to guide the person through a process of putting on the apparatus.

23. The method for presenting voice messages according to claim 13, wherein
said signal processing component is configured to identify or predict hypoglycaemic seizure in said person based on said analysis; and
said selecting step comprises selecting from amongst plural voice messages a voice message for providing said person with information including instructions regarding actions to be performed in order to avoid hypoglycaemic seizure.

24. A portable EEG monitoring apparatus, said apparatus comprising:
an EEG pick-up component configured to measure at least one EEG signal from a person carrying the apparatus,
a signal processor configured to analyze said at least one EEG signal and to identify or predict predetermined biological incidents in said person based on said analysis,
a decision component configured to decide when information is to be presented to said person, wherein said information is one of first and second types, wherein said decision component decides that information of said first type relates to a health state and should be presented to said person only after a first interval (T2) has elapsed since information of said first type was last presented to and acknowledged by said person, and decides that information of said second type should be presented to said person only after a second interval (T3) has elapsed since information of said second type was last presented to said person, and said first interval is shorter than said second interval, a message selector configured to select a voice message providing said person with the information, and an acoustic transducer for presenting the selected voice message to the person as a spoken voice message, where said apparatus is adapted to present the voice message in the ear of the person, said apparatus further comprising:

an acknowledgement component whereby the person carrying the apparatus can acknowledge the presented spoken voice message, the spoken voice message being repeated and the volume thereof increased with each repetition until it is acknowledged; and a user input by which said person can adjust multiple criteria for deciding if said information should be provided to said person, wherein said multiple criteria include at least the first interval (T2), and a time interval (T1) defining an interval at which an unacknowledged message of said first type is repeated until acknowledged by said user, wherein (T1) is of duration less than said first interval.

25. The apparatus according to claim 24, wherein said multiple criteria include at least one alarm threshold.

* * * * *